(12) United States Patent
Isozaki

(10) Patent No.: US 10,502,630 B2
(45) Date of Patent: Dec. 10, 2019

(54) TEMPERATURE MEASUREMENT DEVICE AND TEMPERATURE MEASUREMENT METHOD

(71) Applicant: Topcon Corporation, Itabashi-Ku, Tokyo (JP)

(72) Inventor: Hisashi Isozaki, Tokyo (JP)

(73) Assignee: Topcon Corporation, Itabashi-ku, Tokyo (JP)

(*) Notice: Subject to any disclaimer, the term of this patent is extended or adjusted under 35 U.S.C. 154(b) by 134 days.

(21) Appl. No.: 15/712,264

(22) Filed: Sep. 22, 2017

(65) Prior Publication Data
US 2018/0087968 A1 Mar. 29, 2018

(30) Foreign Application Priority Data
Sep. 27, 2016 (JP) ................... 2016-188480

(51) Int. Cl.
*G01J 5/00* (2006.01)
*A01K 9/00* (2006.01)
(Continued)

(52) U.S. Cl.
CPC ............ *G01J 5/0025* (2013.01); *A01K 9/00* (2013.01); *A01K 29/005* (2013.01); *G01J 5/522* (2013.01);
(Continued)

(58) Field of Classification Search
CPC .. G01J 5/0025; G01J 5/522; G01J 2005/0048; G01J 2005/0077;
(Continued)

(56) References Cited

U.S. PATENT DOCUMENTS

| 4,502,416 A | * | 3/1985 | Keysell ............... A01K 5/0283 119/51.11 |
| 5,333,784 A | * | 8/1994 | Pompei .................... G01J 5/04 236/91 C |

(Continued)

FOREIGN PATENT DOCUMENTS

| JP | 2005515872 A | 6/2005 |
| WO | 03064987 A1 | 8/2003 |
| WO | 2012078054 A1 | 6/2012 |

OTHER PUBLICATIONS

Hoffman et al., "6.1 Monitoring the Body Temperature of Cows and Calves with a Video-Based Infrared Thermography Camera"; Wageningen Academic Publishers; May 2015; 2 pgs.
(Continued)

*Primary Examiner* — Lisa M Caputo
*Assistant Examiner* — Philip L Cotey
(74) *Attorney, Agent, or Firm* — Chiesa Shahinian & Giantomasi PC

(57) ABSTRACT

The temperature measurement device includes a thermography 20 for measuring a temperature distribution of a predetermined range in a non-contact manner; a calibrator 21 including at least one heater 30 able to generate heat to a preset temperature; thermistors 32a to 32d provided on installation points on the calibrator 21, and measuring temperatures at the installation points, the installation points having different temperatures; and a controller 22 for calibrating a first temperature measurement result obtained from a temperature distribution of a range covering an object (an eye E of a calf C) measured by the thermography 20, based on temperature differences between a second temperature measurement result obtained from a temperature distribution of a range covering the calibrator 21 measured by the thermography 20 and a third temperature measurement
(Continued)

result obtained from a temperature distribution of the calibrator 21 measured by the thermistors 32*a* to 32*d*.

3 Claims, 6 Drawing Sheets

(51) Int. Cl.
*A01K 29/00* (2006.01)
*G01J 5/52* (2006.01)

(52) U.S. Cl.
CPC ............... *G01J 2005/0048* (2013.01); *G01J 2005/0077* (2013.01); *G01J 2005/0085* (2013.01)

(58) Field of Classification Search
CPC .... G01J 2005/0085; G01J 5/524; A01K 9/00; A01K 29/005
See application file for complete search history.

(56) References Cited

U.S. PATENT DOCUMENTS

| | | | |
|---|---|---|---|
| 5,628,929 A * | 5/1997 | Klosterman | G05D 23/1917 219/209 |
| 6,360,691 B1 * | 3/2002 | Laue | A01K 5/0216 119/57.92 |
| 7,336,987 B2 | 2/2008 | Laurence et al. | |
| 8,303,514 B2 | 11/2012 | Laurence et al. | |
| 8,447,385 B2 * | 5/2013 | Sterzer | A61B 5/01 600/430 |
| 8,789,494 B2 * | 7/2014 | Thompson | A01J 5/007 119/14.02 |
| 8,948,850 B2 * | 2/2015 | Roth | A61B 5/6887 600/309 |
| 9,534,958 B1 * | 1/2017 | Lhamon | G01J 5/0025 |
| 2003/0142723 A1 | 7/2003 | Laurence et al. | |
| 2004/0022297 A1 * | 2/2004 | Tabata | G01J 5/02 374/120 |
| 2004/0254472 A1 | 12/2004 | McQuilkin | |
| 2005/0220170 A1 * | 10/2005 | Tokita | G01K 1/16 374/163 |
| 2008/0194983 A1 | 8/2008 | Laurence et al. | |
| 2010/0265986 A1 * | 10/2010 | Mullin | G01J 5/0003 374/1 |
| 2012/0178077 A1 * | 7/2012 | DeCastro | G01K 11/06 435/3 |
| 2012/0289855 A1 * | 11/2012 | Bieberich | G01K 1/165 600/549 |
| 2013/0319336 A1 * | 12/2013 | Thompson | A01J 5/007 119/14.02 |
| 2016/0334284 A1 * | 11/2016 | Kaplun Mucharrafille | G01K 15/005 |

OTHER PUBLICATIONS

Extended European Search Report dated Feb. 9, 2018, in connection with European Patent Application No. 17192647.0, 9 pgs.

* cited by examiner

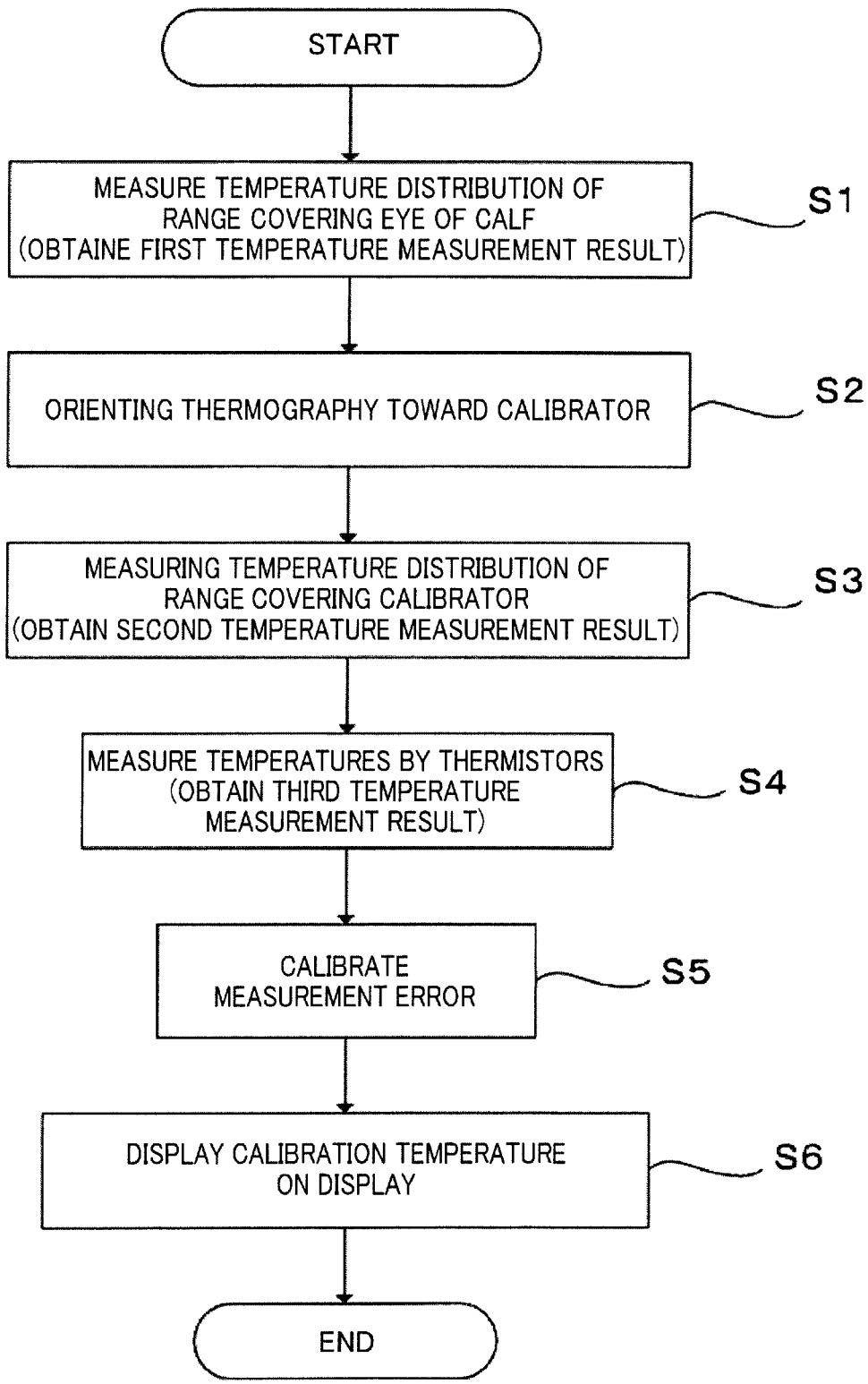

TEMPERATURE MEASUREMENT DEVICE AND TEMPERATURE MEASUREMENT METHOD

CROSS-REFERENCE TO RELATED APPLICATION

This application claims priority to Japanese Patent Application No. 2016-188480 filed on Sep. 27, 2016, the entire disclosure of which is incorporated by reference herein.

BACKGROUND

The present disclosure relates to a temperature measurement device and a temperature measurement method for measuring a body temperature of an animal such as livestock.

To measure a body temperature of an animal such as cattle in a conventional way, a contact thermometer such as a medical thermometer was required to be inserted into a rectum or a mouth and kept in a fixed time period in a fixed position. Thus, both the operator and the animal had high stress and took hard effort.

For this reason, a technique for using a non-contact thermometer such as a thermography etc. to measure a body temperature of an animal apart from the body thereof has been developed (see Japanese Unexamined Patent Publication (Japanese Translation of PCT Application No. 2005-515872).

SUMMARY

However, a typical non-contact thermometer is easily influenced by an external environment such as a wind, and a measurement error (e.g., ±2° C.) is also likely to occur. Such a measurement error occurring in measuring a body temperature causes a reduction in the reliability of health care.

Embodiments of the present disclosure are intended to solve such a problem, and it is an object thereof is to provide a temperature measurement device and a temperature measurement method which can reduce stress and effort of an operator and a target animal, and improve the reliability of measurement of an animal's body temperature.

To achieve the object, the temperature measurement device of an embodiment of the present disclosure is a temperature measurement device for measuring a body temperature of an animal in a non-contact manner apart from a body of the animal, the temperature measurement device comprising: a first temperature measurement portion for measuring a temperature distribution of a predetermined range in a non-contact manner; a calibrator including at least one heater able to generate heat to a preset temperature; second temperature measurement portions provided on installation points on the calibrator, and measuring temperatures at the installation points, the installation points having different temperatures; and a controller for calibrating a first temperature measurement result obtained from a temperature distribution of a range covering an object measured by the first temperature measurement portion, by comparing a second temperature measurement result obtained from a temperature distribution of a range covering the calibrator measured by the first temperature measurement portion with temperatures of respective points of a third temperature measurement result obtained from a temperature distribution of the calibrator measured by the second temperature measurement portions.

To achieve the object, the temperature measurement method of an embodiment of the present disclosure is a temperature measurement method for measuring a body temperature of an animal in a non-contact manner apart from a body of the animal, the temperature measurement method comprising: a first temperature measurement step for making a first temperature measurement portion measure a temperature distribution of a range covering an object, the first temperature measurement portion for measuring a temperature distribution of a predetermined range in a non-contact manner; a second temperature measurement step for making the first temperature measurement portion measure a temperature distribution of a range covering a calibrator including a heater able to generate heat to a preset temperature; a third temperature measurement step for making second temperature measurement portions measure a temperature distribution of the calibrator, the second temperature measurement portions being provided on installation points on the calibrator and measuring temperatures at the installation points, the installation points having different temperatures; and a calibration step for calibrating a first temperature measurement result obtained from the first temperature measurement step based on temperature differences between a second temperature measurement result obtained from the second temperature measurement step and a third temperature measurement result obtained from the third temperature measurement step.

An embodiment of the present disclosure including the above techniques can reduce stress and effort of an operator and a target animal, and improve the accuracy of measurement of an animal's body temperature.

BRIEF DESCRIPTION OF THE DRAWINGS

FIG. 3 is a flow chart showing a temperature measurement control routine executed by a controller of the temperature measurement device of the embodiment.

DETAILED DESCRIPTION

Embodiments of the present disclosure will be described below with reference to the drawings.

Figure 1:
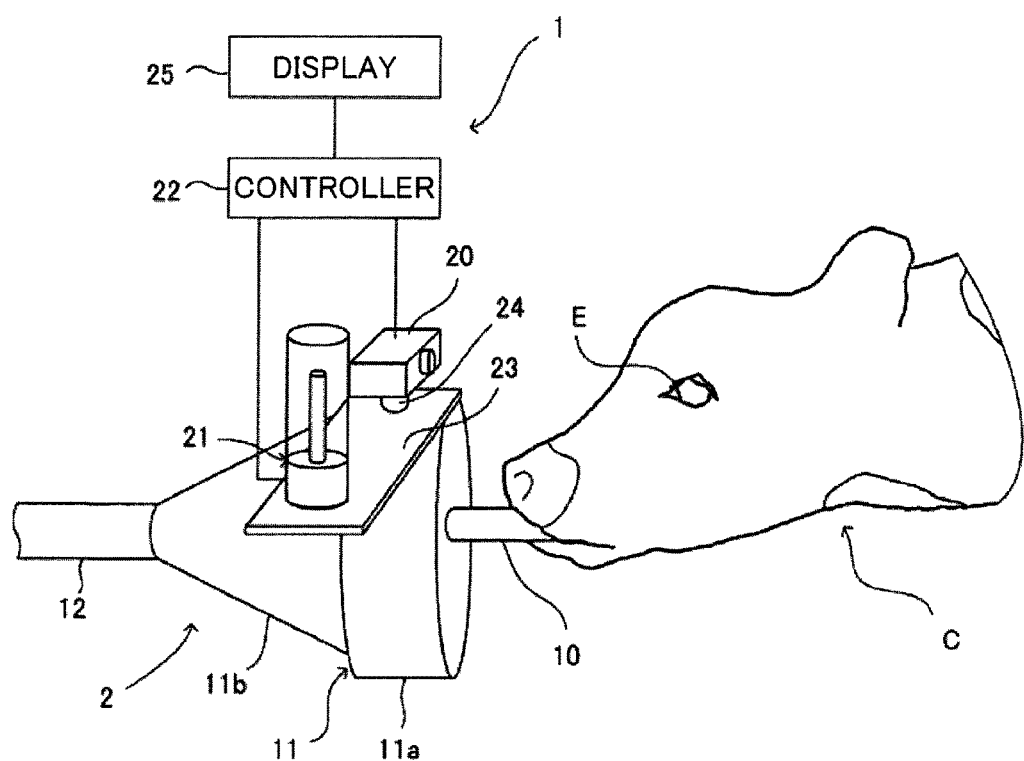
FIG. 1 is an overall view of a temperature measurement device 1 according to one embodiment of the present disclosure.
Figure 2:
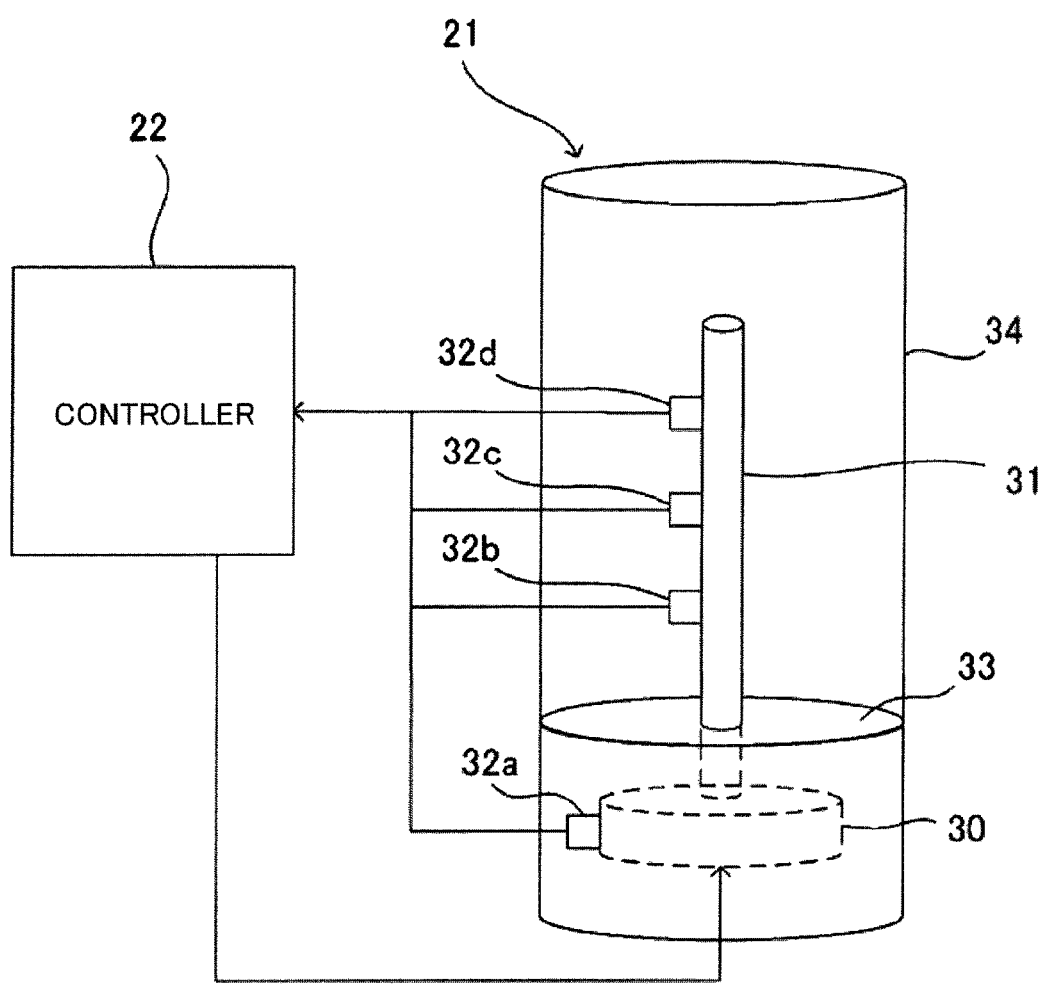
FIG. 2 is a schematic view of a calibrator of one embodiment of the present disclosure.

FIG. 1 is an overall view of a temperature measurement device 1 according to one embodiment of the present disclosure. FIG. 2 is a schematic view of a calibrator.

The temperature measurement device 1 measures a body temperature of a target animal in a non-contact manner apart from the body thereof. In this embodiment, the target animal is a calf C, and an eye E having a surface temperature indicating a high correlation with a deep body temperature is a target object. Most of the temperature measurement device 1 is provided on a nursing unit 2 (a feed provider) for supplying milk as feed of the calf C.

The nursing unit 2 includes an artificial nipple 10 suckled by the calf C, a main body 11 supporting the artificial nipple 10, and a transportation pipe 12 transporting milk from a milk tank (not shown) to the main body 11. The main body 11 includes a cylinder 11a having an end surface having a center supporting the artificial nipple 10, and a cone 11b conically extending from the other end of the cylinder 11a to the transportation pipe 12.

The temperature measurement device 1 principally includes a thermography (a first temperature measurement portion) 20, a calibrator 21, and a controller 22. The thermography 20 and the calibrator 21 are provided on an upper portion of the cylinder 11a of the main body 11 of the nursing unit 2 via a support plate 23 which is plate-like in shape. The support plate 23 extends in a horizontal direction perpendicular to an extension direction of the artificial nipple 10, and has one end fixed on the upper portion of the cylinder 11a.

The thermography 20 is a camera which, based on the amount of infrared rays emitted from a target object, obtains, in a non-contact manner, thermal images showing the temperature distribution of a predetermined range. The thermography 20 is provided on the support plate 23 via a rotation driver 24 which is rotatable in the horizontal direction.

On the other hand, the calibrator 21 is provided on the other end of the support plate 23. Note that the thermography 20 and the calibrator 21 are positioned such that the distance between the thermography 20 and the calibrator 21 is almost equal to the distance from the thermography 20 to the eye of the calf C sucking the artificial nipple 10.

As illustrated in FIG. 2, the calibrator 21 includes a heater 30 and a rod-like heat conductor 31 coupled to the heater 30. The heater 30 and a plurality of points of the heat conductor 31 are provided with thermistors (second temperature measurement portions) 32a to 32d.

The heater 30 is covered with a case 33 which is a cylindrical heat insulator having a bottom. The heat conductor 31 protrudes upward from an upper surface of the case 33. Further, the case 33 has an outer periphery from which a cylindrical cover 34 having an opened upper portion extends upward. The cover 34 is made of a transparent material through which infrared rays transmit. The cover 34 has a windproof function to protect the heat conductor 31 from wind.

The heater 30 is a Peltier device for example, which can generate heat to a preset temperature. The heat conductor 31 is a rod made of copper for example, which conducts a temperature of the heater 30. The heat conductor 31 has a temperature gradient such that an end portion thereof closer to the heater 30 has a highest temperature, and the temperature gradually decreases toward the other end. The heat conductor 31 has a length and thickness determined such that the temperature gradient is at least in the range of body temperatures of a target animal.

The heat conductor 31 is provided with the thermistors 32b to 32d, which are generally evenly spaced in the longitudinal direction of the heat conductor 31. Then, the thermistors 32a to 32d each measure a temperature of the respective installation point. While the four thermistors are provided in this embodiment, at least one thermistor on the heater and one thermistor on the heat conductor only have to be provided. An increase in the number of thermistors leads to an increase in the accuracy. However, even if a small number of thermistors are provided, the temperature of the respective point can be estimated based on the temperature of heat generated by the heater and the configuration of the heat conductor.

The thermography 20, the rotation driver 24, the heater 30, and the thermistors 32a to 32d are communicatively connected with the controller 22. The controller 22 is a personal computer for example, which, for example, obtains, stores, and computes the temperature distribution information measured by the thermography 20 and the temperature information measured by the thermistors 32a to 32d. Depending on the results, the controller 22 performs driving control of the rotation driver 24 and temperature setting of the heater 30.

The controller 22 is also connected to a display 25. The display 25 is a flat panel display (e.g., a LCD) or a CRT display.

To measure a body temperature of a calf in a non-contact manner apart from the body thereof, the controller 22 makes the thermography 20 measure a temperature of a target object, which is the eye of the calf C drinking milk (eating feed) via the nursing unit 2. The controller 22 also makes the calibrator 21 calibrate the measured temperature. As such, the controller 22 performs the temperature measurement control.

Figure 4A:
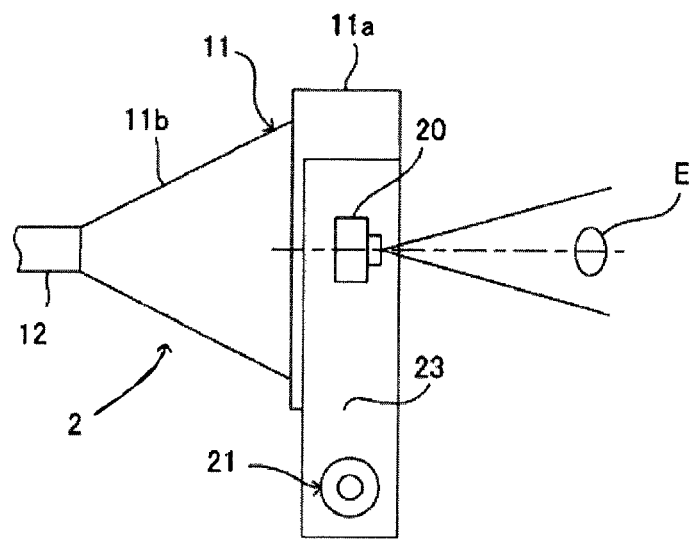
FIG. 4A is a schematic top view showing that a thermography is oriented toward a target object.
Figure 4B:
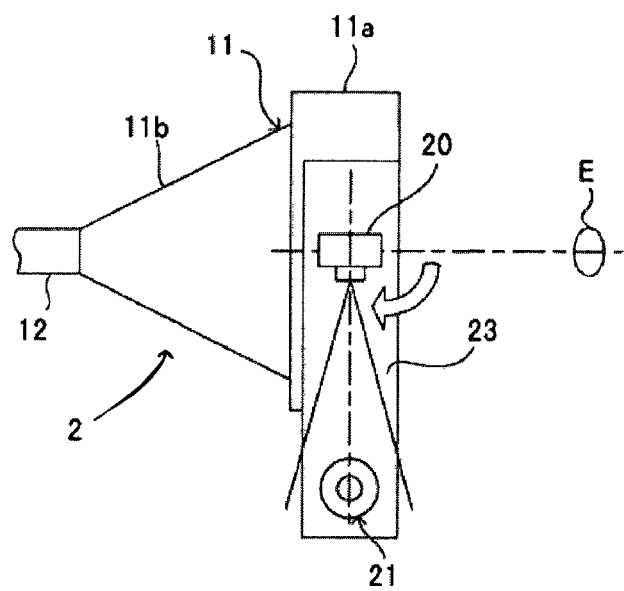
FIG. 4B is a schematic top view showing that the thermography is oriented toward the calibrator.
Figure 5A:
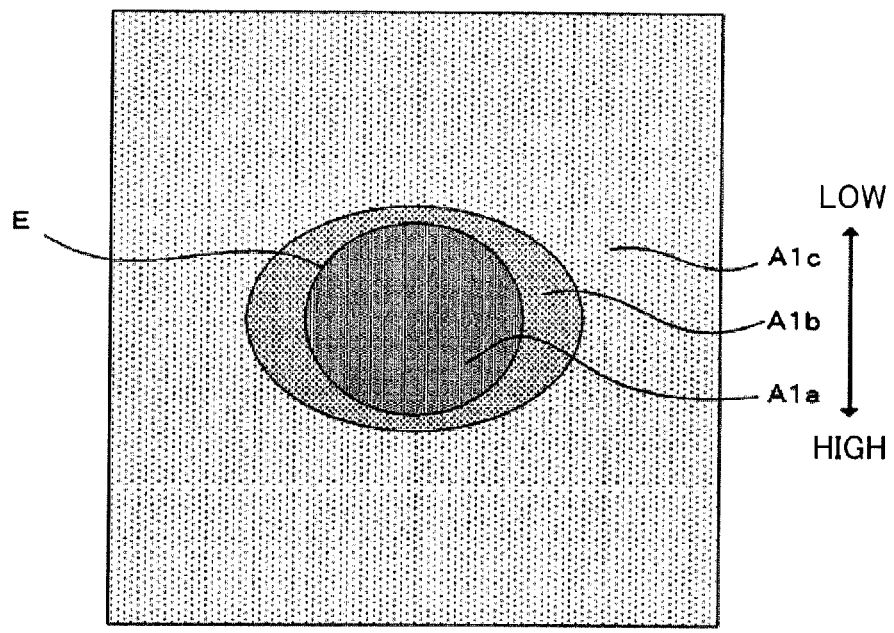
FIG. 5A is an illustration of an example of a temperature distribution of a calf's eye.
Figure 5B:
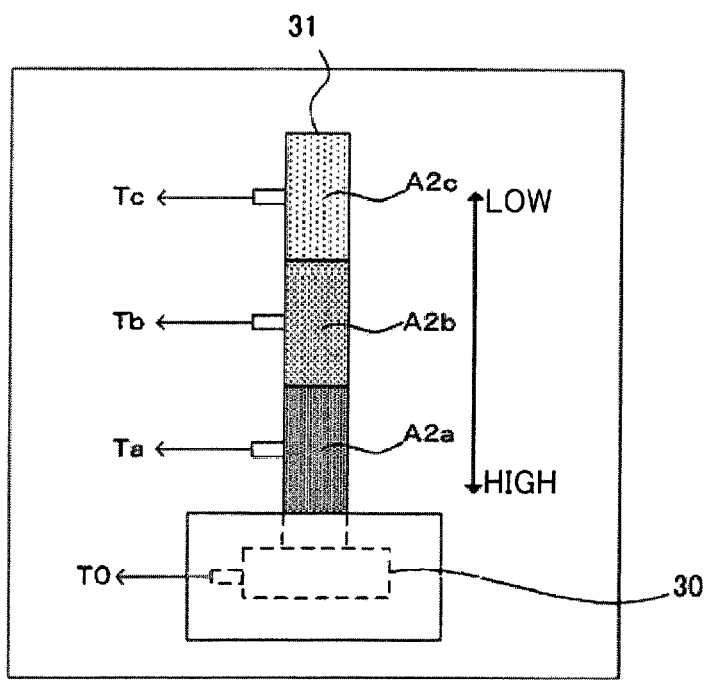
FIG. 5B is an illustration of an example of a temperature distribution of the calibrator.

Specifically, FIG. 3 is a flow chart showing a temperature measurement control routine executed by the controller of the temperature measurement device of this embodiment. FIG. 4A is a schematic top view showing that the thermography is oriented toward the target object. FIG. 4B is a schematic top view showing that the thermography is oriented toward the calibrator. FIG. 5A is an illustration of an example of a temperature distribution of the calf's eye. FIG. 5B is an illustration of an example of a temperature distribution of the calibrator. The descriptions will be provided along the flow chart in FIG. 3, with reference to FIGS. 4 and 5 as well.

First, the controller 22 starts a temperature measurement control triggered when, for example, the calf C sucks the artificial nipple 10 of the nursing unit 2. The controller 22 also makes the heater 30 generate heat to a given temperature in advance. This given temperature is higher than a body temperature of the calf C for example, and maintained in the range of ±0.1° C. by feedback control.

In Step S1, the controller 22 makes the thermography 20 measure the temperature distribution of a range covering the eye E of the calf C (a first temperature measurement step). The temperature distribution measured here is hereinafter referred to as a first temperature measurement result. Specifically, as illustrated in FIG. 4A, the thermography 20 is oriented toward the front direction where the artificial nipple 10 is provided, such that the eye E of the calf C is covered in the measurement range. Then, as illustrated in FIG. 5A, a thermal image of the temperature distribution covering the eye E is obtained. The thermography 20 provides colors varying with the temperature level. For example, in FIG. 5A, the eye E (a range A1a) is shown in a warm color (e.g., a red). The surrounding area of the eye E (a range A1b) is shown in an intermediate color (e.g., a green). The external area of the surrounding area of the eye E (a range A1c) is shown in a cold color (e.g., a blue). A warmer color indicates a higher temperature, and a colder color indicates a lower temperature. While FIGS. 5A and 5B show the temperature range in the three levels to simplify the descriptions, the temperature range is divided into more in practice.

Next, in Step S2, the controller 22 controls the rotation driver 24 to orient the thermography 20 toward the calibrator 21. Specifically, as illustrated in FIG. 4B, the thermography is rotated clockwise in top view by 90° to face the calibrator 21.

In Step S3, the controller 22 measures the temperature distribution of a range covering the calibrator 21 (a second temperature measurement step). The temperature distribution measured here is hereinafter referred to as a second temperature measurement result. Specifically, the thermography 20 is oriented toward the calibrator 21 in Step S2 such that the calibrator 21 is covered in the measurement range. Then, as illustrated in FIG. 5B, a thermal image of the temperature distribution covering the calibrator 21 is obtained. FIG. 5B illustrates the heat conductor 31 where a lower range A2a close to the heater 30 is shown in a warm color, a middle range A2b is shown in an intermediate color, and an upper range A2c is shown in a cold color (e.g., a blue).

In Step S4, the controller 22 makes the thermistors 32a to 32d measure temperatures (a third temperature measurement step). Specifically, as illustrated in 5B, the thermistors 32b to 32d on the heat conductor 31 measure temperatures at the respective points to obtain the temperature distribution of the heat conductor 31. The temperature distribution measured here is hereinafter referred to as a third temperature measurement result. In FIG. 5B, the heat conductor 31 includes a lower portion provided with the thermistor 32b measuring a temperature Ta, a middle portion provided with the thermistor 32c measuring a temperature Tb, and an upper portion provided with the thermistor 32d measuring a temperature Tc. Note that the controller 22 uses a temperature TO measured by the thermistor 32a provided on the heater 30 in order to conduct feedback control for maintaining a temperature of the heater 30.

Next, in Step S5, the controller 22 calibrates a measurement error of the first temperature measurement result by comparing the second temperature measurement result with the temperatures of the respective points of the third temperature measurement result (a calibration step). Specifically, the temperature differences between the temperatures corresponding to ranges A2a to A2c in FIG. 5B of the second temperature measurement result and the measurement temperatures Ta to Tc corresponding to the respective ranges of the third temperature measurement result are calculated as calibration values. Then, the temperature of the range A1a of the eye which is a target object in the first temperature measurement result is calibrated with the respective calibration value to calculate a calibration temperature.

In Step S6, the controller 22 makes the display 25 display at least the calibration temperature of the eye E calibrated in Step S5, and ends the routine. Note that the display 25 might also display the first temperature measurement result, the second temperature measurement result, and the third temperature measurement result, or might display the other information.

As such, the temperature measurement device 1 can obtain an accurate calibration temperature of the eye E by using the calibrator 21 for the temperature distribution of the first temperature measurement result covering the eye E of the calf C measured with the thermography 20. Thus, the measurement of a body temperature in a non-contact manner can reduce stress and effort of an operator and a target animal. In addition, while the measurement of a body temperature contains a large measurement error, the reliability of measurement of a body temperature with the thermography 20 can be improved.

The calibrator 21 of this embodiment includes the heater 30 and the heat conductor 31. The thermography 20 measures the heat conductor 31 to obtain the second temperature measurement result. The thermistors 32b to 32d are provided on the heat conductor 31 to obtain the third temperature measurement result. Thus, the measurement result of the thermography 20 can be easily calibrated with the single heater 30.

In this embodiment, a temperature of the eye E of the calf C is measured to measure a body temperature of the calf C where the eye E has a surface temperature indicating a high correlation with a deep body temperature thereof. Thus, the measurement of a body temperature in the non-contact manner can also provide high reliability of health care.

The temperature measurement device 1 is also provided on the nursing unit 2 (the feed provider) to measure a temperature of the eye E of the calf C drinking milk. Thus, the calf C is not constrained only for measurement of a body temperature, and a temperature of the eye E can be measured in a natural state. This can reduce further stress and effort of an operator and a target animal.

Thus, the temperature measurement device and the temperature measurement method of this embodiment can reduce stress and effort of an operator and a target animal, and improve the accuracy of measurement of an animal's body temperature.

The description of the embodiment of the present disclosure is now ended, but the aspect of the present disclosure is not limited to this embodiment.

Figure 6:
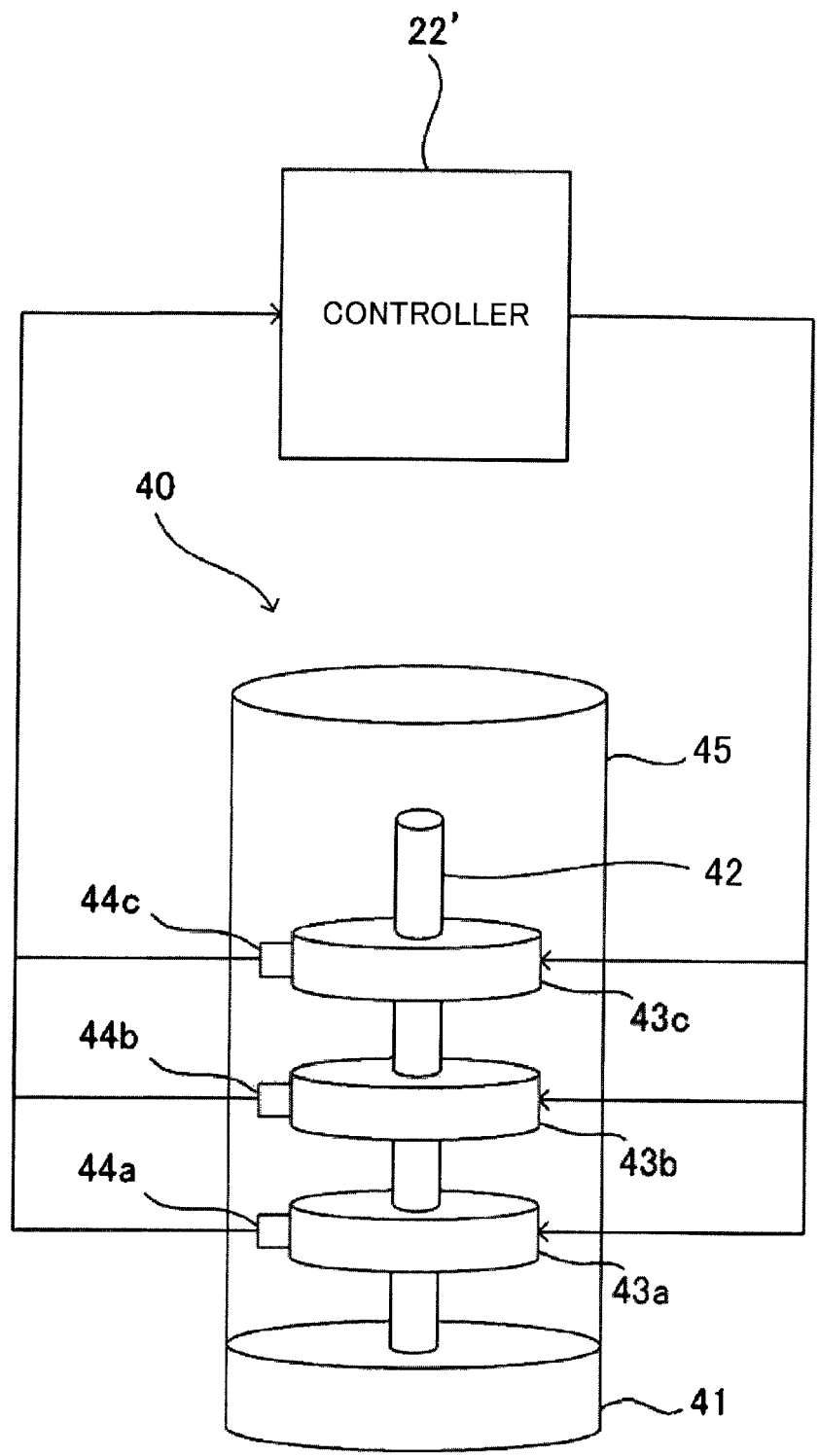
FIG. 6 is a schematic view of a calibrator of a modified example of the present disclosure.

For example, FIG. 6 is a schematic view of a calibrator of a modified example of the present disclosure. The modified example of the present disclosure will be described with reference to the drawing. Note that the components except for the calibrator are the same as those of the above-described embodiment, and labeled with the same reference characters. The detailed descriptions thereof will be omitted.

FIG. 6 illustrates a calibrator 40 including a base 41 from which a heat insulation rod 42 extends upward. The heat insulation rod 42 is provided with heaters 43a to 43c spaced apart. The heaters 43a to 43c are provided with thermistors 44a to 44c, respectively. Similarly to the above-described embodiment, a cover 45 is provided.

The heaters 43a to 43c and the thermistors 44a to 44c are connected to a controller 22'. The controller 22' sets temperatures of the heaters 43a to 43c such that the temperatures are different from each other. For example, the controller 22' sets the temperature of the lower heater 43a to an upper limit of a body temperature of a target animal. The controller 22' also sets the temperature of the middle heater 43b to a middle body temperature of the target animal. The controller 22' also sets the temperature of the upper heater 43c to a lower limit of the body temperature of the target animal. Note that the number of heaters and thermistors only has to be at least two for each, but not limited to that number.

After obtaining a first temperature measurement result, the controller 22' makes thermography 20 measure the temperature distribution of a range covering the calibrator 40 to obtain a second temperature measurement result. Then, the controller 22' makes the thermistor 44a to 44c measure temperatures to obtain a third temperature measurement result. As such, the controller 22' can perform the temperature measurement control similarly to the above-described embodiment.

In this modified example, the calibrator 40 includes the heaters 43a to 43c having the thermistors 44a to 44c, respectively. Thus, the controller 22' can set and manage the temperatures of the heaters 43a to 43c. Thus, more precise calibration can be performed.

In addition, in the above-described embodiment and the modified example, after the thermography 20 measures the temperature distribution of the object (S1), the temperature distribution of the calibrator 21, 40 is measured (S3) and the temperature is measured by the thermistor (S4). However, the order is not limited to this one. For example, first, the measurement of the temperature distribution of the calibrator and the measurement of the temperature by the thermistor might be conducted, and then, the measurement of the temperature distribution of the object by the thermography might be conducted. The measurement of temperatures by the thermistors might be conducted not only at the time of Step S4 but also at a regular basis or at all times.

In the above-described embodiment and the modified example, the rotation driver 24 makes the thermography 20 driven and rotated to measure the temperature distribution of the eye E and the calibrator 21. However, the layout of the thermography and the calibrator is not limited to this one. For example, the calibrator might be arranged such that the thermography has a measurement range covering both the target object and the calibrator. Consequently, the present disclosure can be achieved without the rotation driver, and more efficient calibration can be performed.

In the above-described embodiment and the modified example, the controller 22 starts the temperature measurement control triggered when the calf C sucks the artificial nipple 10 of the nursing unit 2. However, the trigger for the start of the temperature measurement control is not limited to this one.

In the above-described embodiment and the modified example, the temperature measurement device 1 is provided on the nursing unit 2. However, the temperature measurement device is not limited to the nursing unit. The temperature measurement device might be used singly, or provided on another feed provider.

In the above-described embodiment and the modified example, the target animal to be measured is the calf C, and the target object is the eye E. However, the target animal and the target object to be measured by the temperature measurement device are not limited to these ones. For example, other livestock such as a pig might be a target animal. An object other than the eye might be a target object as long as the target object has a surface temperature indicating a high correlation with a deep body temperature thereof.

What is claimed is:

1. A temperature measurement device for measuring a body temperature of an animal in a non-contact manner apart from a body of the animal, the temperature measurement device comprising:
    a feed provider for providing the animal with feed;
    a first temperature measurement portion for measuring a temperature distribution of a predetermined range in a non-contact manner;
    a calibrator including a single heater able to generate heat to a preset temperature and including a heat conductor conducting heat from the single heater and having a temperature gradient such that a part of the heat conductor closer to the single heater has a highest temperature, and the temperature decreases away from the single heater;
    second temperature measurement portions provided on installation points on the heat conductor, and measuring temperatures at the installation points; and
    a controller for calibrating a first temperature measurement result obtained from a temperature distribution of a range covering an object measured by the first temperature measurement portion when the animal eats feed via the feed provider, by comparing
        a second temperature measurement result obtained from a temperature distribution of a range covering the calibrator measured by the first temperature measurement portion with
        temperatures of respective points of a third temperature measurement result obtained from a temperature distribution of the calibrator measured by the second temperature measurement portions.

2. The temperature measurement device of claim 1, wherein
    the feed provider is a nursing unit including an artificial nipple and a main body supporting the artificial nipple, and
    in the main body, the first temperature measurement portion is provided in a higher position than the artificial nipple.

3. A temperature measurement method for measuring a body temperature of an animal in a non-contact manner apart from a body of the animal, the temperature measurement method comprising:
    a first temperature measurement step for making a first temperature measurement portion measure a temperature distribution of a range covering an object when the animal eats feed via a feed provider for providing the animal with the feed, the first temperature measurement portion for measuring a temperature distribution of a predetermined range in a non-contact manner;
    a second temperature measurement step for making the first temperature measurement portion measure a temperature distribution of a range covering a calibrator including a single heater able to generate heat to a preset temperature and including a heat conductor conducting heat from the single heater and having a temperature gradient such that a part of the heat conductor closer to the single heater has a highest temperature, and the temperature decreases away from the single heater;
    a third temperature measurement step for making second temperature measurement portions measure a temperature distribution of the calibrator, the second temperature measurement portions being provided on installation points on the heat conductor and measuring temperatures at the installation points; and
    a calibration step for calibrating a first temperature measurement result obtained from the first temperature measurement step based on temperature differences between a second temperature measurement result obtained from the second temperature measurement step and a third temperature measurement result obtained from the third temperature measurement step.

* * * * *